Figure 1:
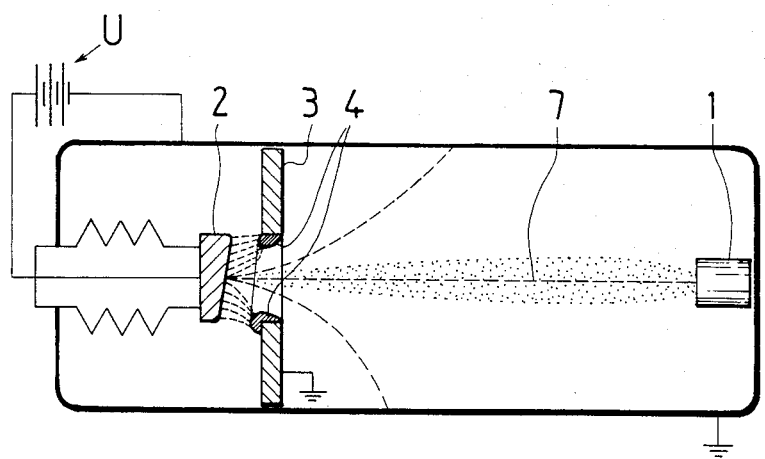

United States Patent [19]

Puumalainen

[11] Patent Number: 4,669,102
[45] Date of Patent: May 26, 1987

[54] METHOD AND DEVICE FOR OPERATING AND FOCUSING TOMOGRAPHIC X-RAY EQUIPMENT

[75] Inventor: Pertti Puumalainen, Kuopio, Finland

[73] Assignee: Puumalaisen Tutkimuslaitos Oy, Finland

[21] Appl. No.: 604,626

[22] PCT Filed: Aug. 19, 1983

[86] PCT No.: PCT/FI83/00059
§ 371 Date: Apr. 18, 1984
§ 102(e) Date: Apr. 18, 1984

[87] PCT Pub. No.: WO84/00848
PCT Pub. Date: Mar. 1, 1984

[30] Foreign Application Priority Data

Aug. 19, 1982 [FI] Finland ................. 822880

[51] Int. Cl.⁴ .................... A61B 6/00; H01J 35/04
[52] U.S. Cl. .................... 378/10; 378/135; 378/137
[58] Field of Search ........... 378/4, 10, 12, 134–138; 250/396 R

[56] References Cited

U.S. PATENT DOCUMENTS

| | | | |
|---|---|---|---|
| 4,045,672 | 8/1977 | Watanabe | 250/360 |
| 4,135,095 | 1/1979 | Watanabe | 250/445 T |
| 4,274,005 | 6/1981 | Yamamura et al. | 378/10 |
| 4,287,425 | 9/1981 | Elliott, Jr. | 250/445 T |
| 4,300,051 | 11/1981 | Little | 378/10 |

FOREIGN PATENT DOCUMENTS

| | | |
|---|---|---|
| 2647220 | 4/1977 | Fed. Rep. of Germany . |
| 0022037 | 3/1981 | Japan ..................... 378/12 |
| 2042790A | 9/1980 | United Kingdom . |
| 1602011 | 11/1981 | United Kingdom . |

*Primary Examiner*—Janice A. Howell
*Attorney, Agent, or Firm*—Pahl, Lorusso & Loud

[57] ABSTRACT

A method and a device for operating and focusing a tomographic x-ray unit using an electron beam and embodying at least one electron gun (1), an anode (2) at which the gun is aimed as well as the x-ray detectors (5) needed to produce a tomographic photograph. In order to construct a device with a sufficiently short exposure time and capable of taking tomographic photographs of fast-moving objects, it is particularly characteristic of this invention that an electron beam (8) emitted by an electron gun (1) is roughly deflected at a hole (4) in the focusing plane (3) which, by means of focusing field lines, draws the electrons into the hole, focuses and accelerates the electron beam which strikes the surface of the anode (2), generating an x-ray source, and that the focusing hole (4) is moved in regard to the anode (2) to generate a series of x-ray sources needed to produce a "layerwise" tomographic photograph of the object under examination.

9 Claims, 7 Drawing Figures

METHOD AND DEVICE FOR OPERATING AND FOCUSING TOMOGRAPHIC X-RAY EQUIPMENT

This invention is concerned with a method and a device designed to direct and focus a tomographic x-ray unit employing an electron beam. Such a unit embodies at least one electron gun and an anode at which it is aimed as well as the x-ray detectors needed to produce a tomographic image.

As a source of radiation, tomographic equipment generally employs an x-ray tube which, during exposure, revolves around the object to be photographed. However, it is not possible to attain such a high rate of revolution for the x-ray tube as to make the equipment suitable for photographing fast-moving organs of the human body, such as the heart region. In practice, exposure times shorter than 1 second cannot be achieved, although exposure times in the order of 0.1 seconds would be required to produce adequate pictures of the heart region, or brain blood circulation when using a contrast medium.

In order to achieve sufficiently short exposure periods, equipment has been devised in which the x-ray tube is replaced with an electron gun generating an electron beam which is focused and magnetically directed at a fixed anode encircling the object.

The problem associated with this construction is how to direct and focus a high-intensity, high-energy electron beam, and how to stabilize the high voltage involved which affects the aforementioned factors.

This invention is an attempt to avoid these problems and to accomplish a method and a device which does not require focusing of the electron gun, nor accurate collimation of the beam. Also, no requirements are set for high-voltage stabilization from the point of view of beam focusing or direction. Beam directing is effected mechanically by means of a focusing ring, and focusing is achieved in the space between the focusing device and the anode where also the actual acceleration of electrons takes place. Characteristic of the method under consideration is that the beam emitted by the electron gun is roughly aimed at a hole in the focusing ring which, by means of focusing field lines, draws the electrons into the hole as well as focuses and accelerates the electron beam, directing it at the anode disc to produce an x-ray source. Moreover, the focusing hole is moved in regard to the anode in such a way as to generate a mobile x-ray sourcewhich produces a "layerwise" photograph of the object under examination.

Another characteristic feature of this method is that the focusing plane has zero potential for which reason the acceleration of the electrons takes place between the focusing surface and the anode. Furthermore, the field lines generated by the potential between the focusing plane and the anode extend partly to the space between the focusing plane and the electron gun, thus drawing the electrons into the focusing hole like a hopper.

Another characteristic feature of this method is that the anode and the focusing plane are in the form of concentric rings, and that the focusing plane is caused to revolve at a uniform speed, and that the electron gun is timed to emit the beam in pulses whereby it hits the anode at evenly spaced points. In addition to a ring-shaped anode and focusing plane, the object is surrounded by a ring of x-ray detectors, for which reason the most appropriate form of the apparatus is that of a funnel or a cylinder.

Furthermore, it is characteristic of the method that several electron guns are mounted along the casing of a basically cylinder-shaped apparatus so that the beams emitted by them are roughly deflected in the direction of the tangent of the casing towards the holes in the focusing plane numbering from one to several to each gun. In this way, each deflected beam is directed at a specific portion of the anode disc. During irradiation, the focusing ring turns a distance equivalent to the distance between two holes. The deflection of the electron beam can be effected as one-level rough deflection which permits the use of two focusing holes to each gun.

Furthermore, it is characteristic of the method based on this invention that, when the focusing ring turns the distance it is supposed to, the electron guns emit a beam in rapid succession in the order determined by the direction of rotation of the focusing ring. In this way, several rounds of electron beam emissions are achieved during exposure. If there are several holes in the focusing ring to each gun, deflection is effected alternatingly through different holes.

Characteristic of a device utilizing one of the advantages offered by this invention is that between the electron guns and the anode there is a rotating focusing ring with one or several holes which directs the electron beam mostly mechanically.

Another characteristic of such a device is that the anode, focusing plane and the x-ray detectors form concentric rings and that the focusing ring can be rotated at a uniform speed.

Moreover, it is characteristic of such a device that several electron guns are mounted along the casing at equal distance from one another, and that in the focusing ring there are one or several holes to each gun, whereby the beams emitted by them can be directed to a specific hole by roughly deflecting the beams in the direction of the tangent of a cylinder-shaped unit.

Figure 2:
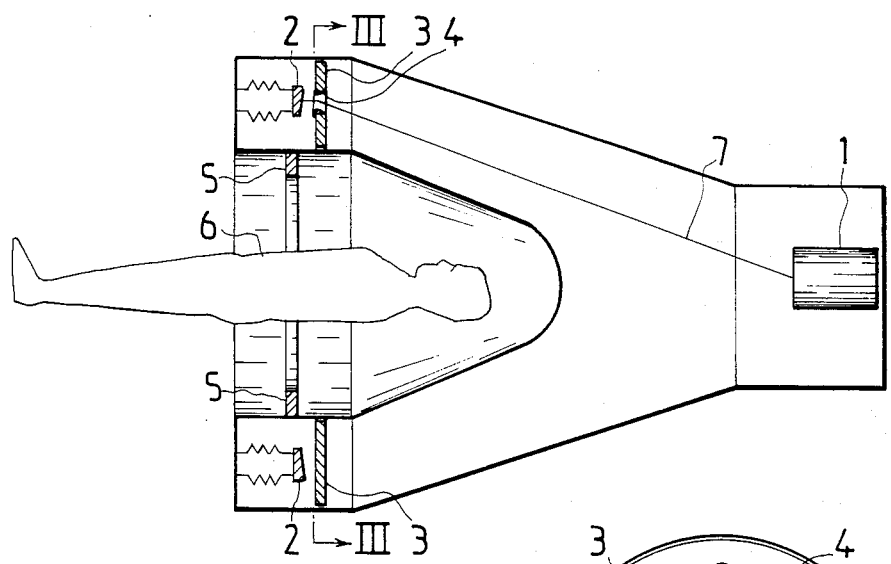

Below, the invention is described in greater detail by means of examples and with reference to enclosed drawings where FIG. 1 presents the principle of operation of the invention;

FIG. 2 provides side view of one of the applications of the invention

Figure 3:
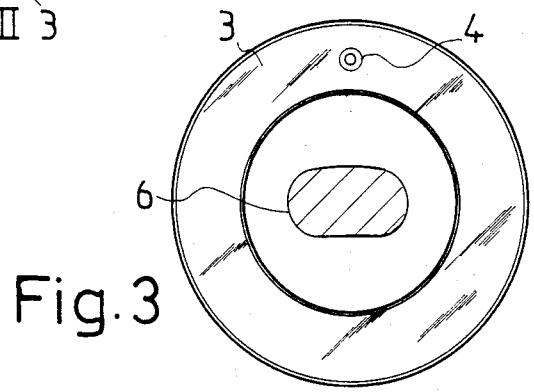

FIG. 3 provides front view of a device presented in FIG. 2

Figure 4:
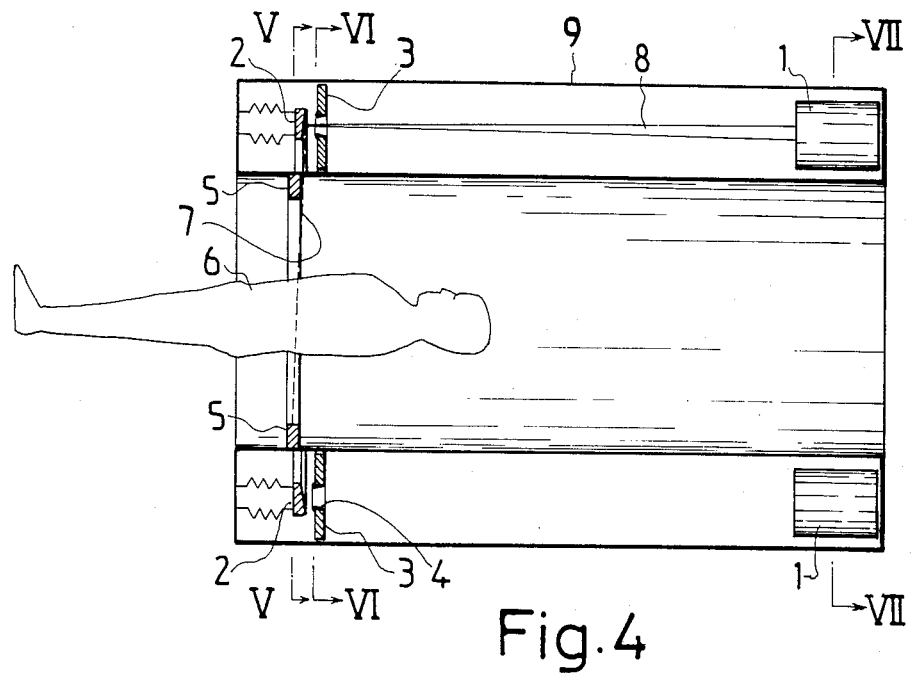

FIG. 4 provides side view of another application of the invention

Figure 5:
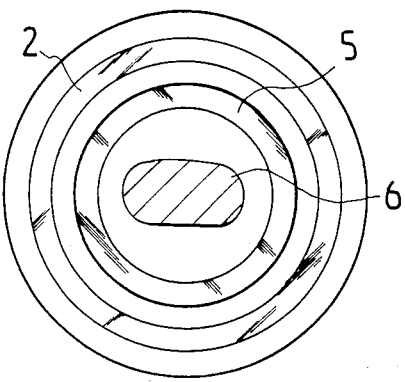

FIG. 5 provides cross-section V—V of the device presented in FIG. 4

Figure 6:
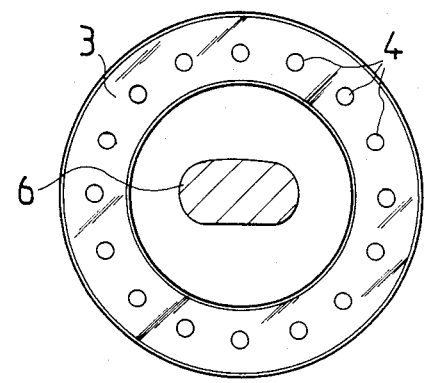

FIG. 6 provides cross-section VI—VI of the device presented in FIG. 4

Figure 7:
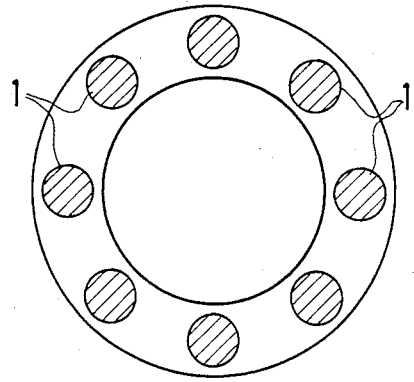

FIG. 7 provides cross-section VII—VII of the device presented in FIG. 4

EXAMPLE 1

Let us consider a simple device exemplifying this invention (FIG. 1). A high-intensity electron gun, the beam of which can be turned on and off by means of internal control voltage, is used as a source of electrons. Between the anode disc (2) and the focusing ring (3) there is a high voltage which generates the field lines (dashed lines in FIG. 1) which focus the electrons by means of specially designed hole (4). Part of the field lines generated by high voltage U extend to the vacuum between the electron gun (1) and the focusing system (3), drawing the electrons (7) into the hole (4) after which they are accelerated.

When the focusing ring (3) is moved across the beam of the electron gun (1) which is alternatingly being turned off and on, a series of x-ray sources is produced on the surface of the anode (2) in the direction of rotation of the ring.

EXAMPLE 2

Using the principle described above, it is possible to construct the tomographic device presented in FIG. 2. The electron gun (1) is mounted at the top of a conical vacuum tube, and the anode (2) and focusing discs (3) are formed into rings surrounding the object (6) to be photographed. By rotating the one-holed (4) focusing disc (3) one round in 0.1 seconds while the electron gun is emitting, say, 1000 high-speed electron pulses and 250 of the 1000 fixed detectors (5) (of the scintillation semiconductor type) on the opposite side of the object (6) are collecting the absorbtion information for each pulse, it is possible to produce a photograph consisting of 500×500 elements.

Such a simple application, however, requires an extremely high-powered electron gun and quick-acting detection elements. The situation can be remedied in two ways (examples 3 and 4):

EXAMPLE 3

The beam (7) emitted by the electron gun (1) is roughly deflected; if, for instance, the beam (7) can be directed at a specific quarter of the cone (FIG. 2), the number of focusing holes can be increased to four. Now the beam can be emitted by directing it at one hole after another. As a result, the focusing ring turns only one fourth of a round during the time the picture is taken, and the focal point shifts only one fourth of the distance required for a one-holed ring, which gives a significantly improved resolution.

EXAMPLE 4

A situation analoguous to Example 3 is obtained by using a cylinder-shaped structure instead of a cone (FIG. 4) and by increasing the number of electron guns (1) as well as the corresponding number of focusing holes (4). This will ensure shorter shooting distance and facilitate the directing of the beam (7).

EXAMPLE 5

An optimum device can be constructed by using a combination of the equipment described in Examples 3 and 4 in which both methods of retarding the focal point are employed. The principle of such a device is presented in FIGS. 4, 5, 6 and 7. The device consists of a cylinder-shaped casing (9) which encircles the object (6) to be photographed. The vacuum cylinder houses 8 electron guns (1), and there are 2 holes in the focusing ring (4) to each gun, totalling 16, and the anode (2) forms a full ring around the object under examination. The detectors (5) are also placed in a ring form around the object.

The beams issuing from the guns are deflected tangentially along the focusing ring, which roughly determines beam direction at the desired hole (4). The guns are triggerred in succession so that when the focusing ring (3) turns a distance equivalent to the distance between two holes, the guns are activated one after the other in the order determined by the direction of rotation of the ring.

If, for example, the exposure time is 0.1 seconds and a photograph consisting of 500×500 elements is required, 1000 bursts of electrons are fired at the anode as described above while 250 detectors located on the opposite side of the object collect absorbtion information on each point. A deflected and pulsed beam emitted by the various guns at the two focusing holes (4) alternatingly travels about 63 times around the anode ring (2) during exposure while the focusing ring turns 1/16 of a round.

Assuming that the length of the ring is 5 m, focal points will be generated at a distance of 5 mm from one another. If irradiation at one point last 50 μs and the collection of data takes another 50 μs, the movement of the focus with a 16-holed ring is merely $\frac{1}{2}\times 1/16\times 5$ mm, or appr. 0.16 mm, which is sufficient not to render the focus inaccurate.

Consequently, an accurate and quick "layerwise" tomographic photograph of the object can be taken with the equipment described above. It is obvious to a professional that the various applications of the invention are not confined to these examples but can vary within the framework of the patent claims presented below.

I claim:

1. A device for directing and focusing an electron beam in a tomographic x-ray unit comprising an elongated electrically conductive housing;
    at least one electron gun for emitting an electron beam adjacent one end of said housing;
    an x-ray emitting anode near the other end of said housing;
    a rotatable electrically grounded focusing ring located adjacent said anode betwwen said anode and said electron gun;
    means for applying a high voltage electric field between said anode and said focusing ring so as to accelerate electrons to said anode, said focusing ring having at least one hole formed therein so as to alter said field such that electrons are focused and forced through said hole on their way from the gun to the anode;
    means for rotating said ring so that electrons are scanned along said anode; and
    means for detecting x-rays emitted by the anode and means for producing a tomographic image.

2. The device of claim 1 wherein said focusing ring has zero potential and wherein the hole in said focusing ring permits field lines generated by high voltage between said focusing ring and said anode to partly extend into a space between said focusing ring and electron gun.

3. The device of claim 1 wherein said anode and said focusing ring are concentric rings, said focusing ring being rotatable at a uniform speed and said electron beam gun being firable at the anode at appropriate intervals and at appropriate points.

4. The device of claim 3 further comprising a substantially cylindrical casing, a plurality of electron beam guns being mounted along said casing, said casing and said guns permitting the electron beams emitted from said electron beam gun to be roughly deflected in a direction of an axis of said casing toward the holes in said focusing plane, said focusing ring including at least one focusing hole for each electron beam gun, and said focusing ring being movable a distance equivalent to a distance between two holes on said ring during exposure.

5. The device of claim 12 wherein when said focusing ring is moved the distance between two holes on said ring, said electron guns being firable in succession in the order determined by the direction of rotation of said focusing ring.

6. A method to produce a tomographic image of a subject comprising:
   placing the subject adjacent an elongated electrically conductive housing;
   firing an electron beam gun located adjacent one end of the housing to produce an electron beam;
   applying a high voltage electric field between an x-ray emitting anode located at the other end of the housing and a rotatable electrically grounded focusing ring having one or more holes adjacent the anode and between the anode and the electron gun so as to accelerate the electron beam to the anode;
   directing the electron beam at one or more holes in the rotatable electrically grounded focusing ring so as to alter the field such that the accelerated electrons are focused and forced through the hole on their way from the gun to the anode;
   rotating the focusing ring having one or more holes relative to the anode so that a moving focal point is generated on the surface of the anode; and
   detecting the x-rays emitted by the anode to produce a tomographic image.

7. The method of claim 6 wherein the rotating step is performed at a uniform speed, the anode and the focusing ring are concentric rings and the firing of the electron beam gun is timed to hit the anode at appropriate points.

8. The method of claim 7 further comprising the step of mounting more than one electron gun along a substantially cylindrical casing, the beams emitted from the guns are roughly deflected in the direction of the axis of the casing towards the holes in the focusing ring and to a specific portion of the anode and the focusing ring turns a distance equivalent to a distance between two holes during the rotation of the focusing plane during exposure.

9. The method of claim 8 wherein as the focusing ring is rotated the pre-determined distance during exposure, the electron beam guns are fired in succession in the order determined by the direction of the rotation of the focusing ring.

* * * * *